United States Patent
Lin et al.

(10) Patent No.: US 10,149,871 B2
(45) Date of Patent: Dec. 11, 2018

(54) **METHOD FOR PREVENTING AND/OR TREATING OSTEOPOROSIS BY USING *STREPTOCOCCUS THERMOPHILUS* TC1633 STRAIN AND ITS METABOLITES**

(71) Applicant: TCI CO., LTD, Taiwan (TW)

(72) Inventors: Yung-Hsiang Lin, Taipei (TW); I-Hui Chen, Taipei (TW); Hui-Hsin Shih, Taipei (TW); Chi-Ying Lee, Taipei (TW)

(73) Assignee: TCI CO., LTD., Taipei (TW)

( * ) Notice: Subject to any disclaimer, the term of this patent is extended or adjusted under 35 U.S.C. 154(b) by 0 days.

(21) Appl. No.: 15/629,076

(22) Filed: Jun. 21, 2017

(65) Prior Publication Data

US 2017/0360851 A1   Dec. 21, 2017

Related U.S. Application Data

(60) Provisional application No. 62/352,777, filed on Jun. 21, 2016.

(51) Int. Cl.
| | | |
|---|---|---|
| *A61K 39/09* | (2006.01) | |
| *A61K 35/744* | (2015.01) | |
| *A61K 9/00* | (2006.01) | |

(52) U.S. Cl.
CPC .......... *A61K 35/744* (2013.01); *A61K 9/0053* (2013.01)

(58) Field of Classification Search
None
See application file for complete search history.

(56) References Cited

U.S. PATENT DOCUMENTS

2015/0290257 A1   10/2015   Lin et al.

FOREIGN PATENT DOCUMENTS

| | | |
|---|---|---|
| CN | 101280286 A | 10/2008 |
| TW | 201538722 A | 10/2015 |

OTHER PUBLICATIONS

Gohel (J Clin Diagn Res. Apr. 2016;10(4):LC05-9).*
Buckley et al (Acta Astronautica (2011), 68(7-8), 731-738),.*
Resta-Lenert et al (FASEB Journal. (Apr. 2008). vol. 22. Experimental Biology Annual Meeting. San Diego, CA, USA. Apr. 5-9, 2008), abstract.*
Resta-Lenert et al (Gastroenterology, (Apr. 2007) vol. 132, No. 4, Suppl. 2, pp. A400). Abstract Only.*
Swanson, Lara, "Probiotics in the Improvement of Bone Density," http://probiotics101.probacto.com/probiotics-in-the-improvement-or-bone-density/), Aug. 30, 2013 (9 pgs.).
Crittenden, R.G., et al., "Synthesis and utilization of folate by yoghurt starter cultures and probiotic bacteria," *International Journal of Food Microbiology*, pp. 217-222 (2003).

* cited by examiner

*Primary Examiner* — Jennifer E Graser

(74) *Attorney, Agent, or Firm* — Christensen, Fonder, Dardi & Herbert PLLC

(57) ABSTRACT

A method for at least one of preventing osteoporosis, treating osteoporosis, delaying bone loss, increasing bone density, and strengthening bones is provided, wherein the method comprises administering to a subject in need an effective amount of *Streptococcus thermophilus* TC1633 strain and/or its metabolites. The *Streptococcus thermophilus* TC1633 strain was deposited at German Collection of Microorganisms and Cell Cultures (Deutsche Sammlung von Mikroorganismen und Zellkulturen GmbH, DSMZ) under the accession number DSM 28121.

12 Claims, 2 Drawing Sheets

(1 of 2 Drawing Sheet(s) Filed in Color)

METHOD FOR PREVENTING AND/OR TREATING OSTEOPOROSIS BY USING *STREPTOCOCCUS THERMOPHILUS* TCI633 STRAIN AND ITS METABOLITES

FIELD OF THE INVENTION

The present invention relates to the uses of *Streptococcus thermophilus* TCI633 strain and/or its metabolites. The invention especially relates to the uses of the *Streptococcus thermophilus* TCI633 strain and/or its metabolites in preventing and/or treating osteoporosis, including the uses of the *Streptococcus thermophilus* TCI633 strain and/or its metabolites in inhibiting osteoclast activation and differentiation. The *Streptococcus thermophilus* TCI633 strain was deposited at German Collection of Microorganisms and Cell Cultures (Deutsche Sammlung von Mikroorganismen und Zellkulturen GmbH, DSMZ) under the accession number DSM 28121.

BACKGROUND OF THE INVENTION

Osteoporosis is a systemic bone disease characterized by bone mass loss and bone tissue structure weakened. Because of the bone mass loss and bone tissue structure weakened, patients with osteoporosis have a higher risk of fracture and often have other complications caused by fracture such as dysfunction, bone deformity, pain, and even death. It is known that bone density will decrease along with age and, for females, the bone density will decrease sharply after amenorrhea. Furthermore, other factors such as thyroid diseases, diabetes, steroid usage, smoking, alcoholism, or intestinal malabsorption may also promote the loss of calcium. Researchers have found that the primary pathological mechanism of decreasing bone density is when the activity of osteoclasts is higher than that of osteoblasts, calcium will move from bone to blood and thus, causes bone calcium loss.

Though appropriate supplement of calcium and exercise are helpful for maintaining bone density, most modern people lack exercise and the supplement of calcium alone cannot effectively decrease the rate of calcium loss or alleviate the pain caused by osteoporosis. Therefore, there is still a need for the art to have effective methods and medicaments for preventing or treating osteoporosis.

The present invention is the results of the research and development addressing the above problem. Inventors of the present invention found that the *Streptococcus thermophilus* TCI633 strain and/or its metabolites can effectively inhibit osteoclast activation and differentiation, and thus, can be used for preventing and/or treating osteoporosis.

SUMMARY OF THE INVENTION

An objective of the present invention is to provide a use of the *Streptococcus thermophilus* TCI633 strain and/or its metabolites in the manufacture of a medicament, wherein the medicament is used for preventing and/or treating osteoporosis, and the *Streptococcus thermophilus* TCI633 strain was deposited at German Collection of Microorganisms and Cell Cultures (Deutsche Sammlung von Mikroorganismen and Zellkulturen GmbH, DSMZ) under the accession number DSM 28121. Preferably, the medicament is used for inhibiting osteoclast activation and/or differentiation, and is provided in a form suitable for oral administration.

Another objective of the present invention is to provide a use of *Streptococcus thermophilus* TCI633 strain and/or its metabolites in the manufacture of a food product, wherein the *Streptococcus thermophilus* TCI633 strain was deposited at German Collection of Microorganisms and Cell Cultures (Deutsche Sammlung von Mikroorganismen und Zellkulturen GmbH, DSMZ) under the accession number DSM 28121, and the food product is used for at least one of delaying bone loss, increasing bone density, and strengthening bones. The food product can be a health food, a nutritional supplement food or a special nutrition food. Preferably, the food product is a health food.

Still another objective of the present invention is to provide a method for at least one of preventing osteoporosis, treating osteoporosis, delaying bone loss, increasing bone density, and strengthening bones, comprising administering to a subject in need an effective amount of *Streptococcus thermophilus* TCI633 strain and/or its metabolites. Preferably, the *Streptococcus thermophilus* TCI633 strain and/or its metabolites are administered to the subject by oral administration.

BRIEF DESCRIPTION OF THE DRAWINGS

The patent application contains at least one drawing executed in color. Copies of this patent with color drawing(s) will be provided by the Patent and Trademark Office upon request and payment of the necessary fee.

DESCRIPTION OF THE PREFERRED EMBODIMENTS

Figure 1:
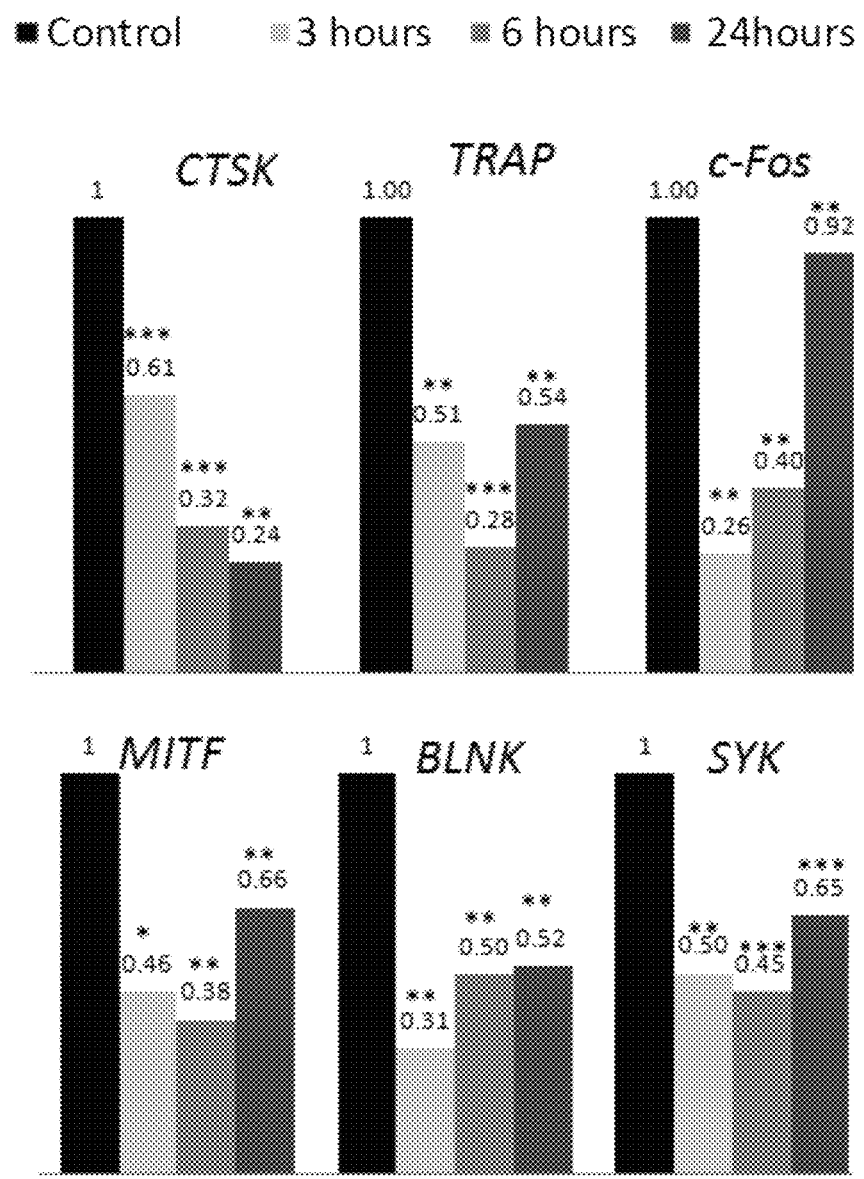
FIG. 1 is the result of an RNA microarray, showing the expression levels of CTSK (Cathepsin K), TRAP (Tartrate-resistant acid phosphatase), c-FOS, MITF (Microphthalmia-associated transcription factor), BLNK (B cell linker) and SYK (Spleen tyrosine kinase) in the peripheral blood mononuclear cells (PBMCs) cultivated with different conditions, wherein the "control group" was cultivated in a medium free of TCI633 strain fermentation supernatant for 24 hours, and the "3 hours group," "6 hours group" and "24 hours group" were carried out as the "control group," but the TCI633 strain fermentation supernatant was separately added into the medium of each group 3 hours, 6 hours and 24 hours before the end of the cultivation.

The following will describe some embodiments of the present invention in detail. However, without departing from the spirit of this invention, the present invention may be embodied in various embodiments and should not be illustrated as limited to the embodiments descried in the specification.

In addition, unless otherwise state herein, the expression "a," "an," "the" or the like recited in the specification of the present invention (especially in the claims) should be interpreted to include both the singular and plural forms. Furthermore, the term "treat" or "treating" recited in the specification should not be construed as treating a subject until the subject is completely recovered, but should include maintaining the progression or symptoms of the diseases in a substantially static state, increasing the recovery rate of a subject, alleviating the severity of a particular condition of illness, or increasing the quality of life for a patient. The term "prevent" or "preventing" recited in the specification refers to inhibiting or preventing a particular condition of illness from breaking out, or maintaining good health in a sensitive subject to tolerate diseases. The term "an effective amount" recited in this specification refers to the amount of the substance that can at least partially alleviate the condition that is being treated in a suspected subject when administered to the subject. The term "subject" recited in this specification refers to a mammalian, including human and non-human animals. The unit "CFU/kg-body weight" recited in this specification refers to the dosage required per kg of body weight.

Osteoporosis causes various inconvenience to a patient's life, and the complications caused thereby can even be mortal. So far, there is still a need for the art to have effective approaches for preventing and/or treating osteoporosis. Inventors of the present invention found that *Streptococcus thermophilus* TCI633 strain and/or its metabolites can effectively inhibit osteoclast activation and differentiation, and thus, can be used for preventing osteoporosis, treating osteoporosis, delaying bone loss, increasing bone density, and/or strengthening bones.

Therefore, the present invention provides the uses of using *Streptococcus thermophilus* TCI633 strain and/or its metabolites in preventing osteoporosis, treating osteoporosis, delaying bone loss, increasing bone density, and/or strengthening bones. The aforementioned uses include: a use of *Streptococcus thermophilus* TCI633 strain and/or its metabolites in the manufacture of a medicament for preventing and/or treating osteoporosis; a use of *Streptococcus thermophilus* TCI633 strain and/or its metabolites in the manufacture of a food product for delaying bone loss, increasing bone density, and/or strengthening bones; a method of preventing osteoporosis, treating osteoporosis, delaying bone loss, increasing bone density, and/or strengthening bones comprising administering *Streptococcus thermophilus* TCI633 strain and/or its metabolites to a subject in need.

The *Streptococcus thermophilus* TCI633 strain's metabolites adopted according to the present invention could be generated by cultivating *Streptococcus thermophilus* TCI633 strain under an environment suitable for its growth. For example, a *Streptococcus thermophilus* TCI633 strain's metabolites-containing liquid could be obtained by cultivating *Streptococcus thermophilus* TCI633 strain in a suitable medium, and then optionally removing the solids, including bacteria, from the medium.

To provide the desired metabolites, any suitable medium could be chosen and used to perform the cultivation of *Streptococcus thermophilus* TCI633 strain, as long as the medium can provide the desired nutrients (e.g., yeast extract, protein and glucose) and conditions (e.g., pH value) for the growth and metabolism of *Streptococcus thermophilus* TCI633 strain. Furthermore, the time period for cultivating *Streptococcus thermophilus* TCI633 strain is not specifically limited, as long as the time period is sufficient for the *Streptococcus thermophilus* TCI633 strain to complete at least one metabolic cycle. For example, in one embodiment of the present invention, *Streptococcus thermophilus* TCI633 strain was cultivated in a MRS medium for 15 hours to let the strain metabolize and generate metabolites.

The present invention could directly use a medium that has undergone the metabolism cycles of *Streptococcus thermophilus* TCI633 strain, which contains the *Streptococcus thermophilus* TCI633 strain and its metabolites. Otherwise, the present invention could use a *Streptococcus thermophilus* TCI633 strain's metabolites-containing liquid, from which the solids such as *Streptococcus thermophilus* TCI633 strain have been removed. Any suitable procedure could be employed to remove the solids, as long as the procedure does not adversely affect the desired effects of the metabolites generated after cultivation. Generally, physical approaches, such as centrifugal separation, filter filtration, precipitation and decantation, could be employed to remove the solids. Optionally, the above operations can be repeated or combined to remove solids (including bacteria) from the medium as much as possible.

Depending on the desired administration manner, the medicament according to the present invention could be provided in any suitable form without specific limitations. For example, the medicament could be administered by an oral route to a subject in need to prevent osteoporosis, treat osteoporosis, delay bone loss, increase bone density, and/or strengthen bones, but the administration is not limited thereby. Depending on the form and purpose, suitable carriers could be chosen and used to provide the medicament, as long as the carriers do not adversely affect the desired effects of *Streptococcus thermophilus* TCI633 strain and/or its metabolites. For example, the carriers could be, but are not limited to excipients, diluents, auxiliaries, stabilizers, absorbent retarders, disintegrants, hydrotropic agents, emulsifiers, antioxidants, adhesives, binders, tackifiers, dispersants, suspending agents, lubricants, hygroscopic agents, etc.

As a dosage form suitable for oral administration, the examples of the carrier include, but are not limited to, water, saline, dextrose, glycerol, ethanol or its analogs, cellulose, starch, sugar bentonite, and combinations thereof. The medicament could be provided in any suitable form for oral administration, such as in the form of a powder (e.g., dried bacteria powder), a tablet (e.g., dragee), a pill, a capsule, granules, a pulvis, a fluid extract, a solution, syrup, a suspension, a tincture, etc.

Optionally, the medicament provided by the present invention could further comprise a suitable amount of additives, such as a flavoring agent, a toner, or a coloring agent for enhancing the palatability and the visual perception of the medicament, and/or a buffer, a conservative, a preservative, an antibacterial agent, or an antifungal agent for improving the stability and storability of the medicament. In addition, the medicament could optionally further comprise one or more other active ingredient(s) (such as calcium supplement, vitamin D, diphosphate, etc.), or be used in combination with a medicament comprising one or more other active ingredient(s), to further enhance the effects of the medicament, or to increase the application flexibility and adaptability of the preparation thus provided, as long as the other active ingredients do not adversely affect the desired effects of *Streptococcus thermophilus* TCI633 strain and/or its metabolites.

Depending on the need, age, body weight, activity level and health conditions of the subject, the medicament provided according to the present invention could be dosed with various administration frequencies, such as once a day, multiple times a day, or once every few days, etc. For example, when the medicament is applied orally to a subject for preventing osteoporosis and/or treating osteoporosis, the dosage of the medicament is at least $8.06 \times 10^8$ CFU (as the TCI633 strain)/kg-body weight per day, preferably ranging from $8.06×10^8$ CFU (as the TCI633 strain)/kg-body weight to $8.06×10^{10}$ CFU (as the TCI633 strain)/kg-body weight per day, and more preferably ranging from $8.06×10^9$ CFU (as the TCI633 strain)/kg-body weight to $8.06×10^{10}$ CFU (as the TCI633 strain)/kg-body weight per day.

The food product according to the present invention could be a health food, a nutritional supplement food or a special nutrition food. It could be provided as dairy products, meat products, breads, pasta, cookies, troche, fruit juices, teas, sport drinks, nutritional drinks, etc., but is not limited thereby. Preferably, the food product according to the present invention is a health food.

Depending on the need, age, body weight, activity level and health conditions of the subject, the health food, nutritional supplement food or special nutrition food provided according to the present invention could be taken in various frequencies, such as once a day, multiple times a day, or once every few days, etc. The amount of *Streptococcus thermophilus* TCI633 strain and/or its metabolites in the health food, nutritional supplement food and special nutrition food provided according to the present invention could be adjusted, preferably to the amount that should be taken daily, depending on the specific population.

The recommended daily dosage, use standards and use conditions for a specific population (e.g., pregnant woman, woman after amenorrhea, and osteoporosis patients), or the recommendations for a use in combination with another food product or medicament could be indicated on the exterior package of the health food, nutritional supplement food and/or special nutrition food provided by the present invention. Thus, it is suitable for the user to take the health food, nutritional supplement food and/or special nutrition food by him- or herself safely and securely without the instructions of a doctor, pharmacist, or related executive.

The present invention further provides a method for at least one of preventing osteoporosis, treating osteoporosis, delaying bone loss, increasing bone density, and strengthening bones, comprising administering to a subject in need an effective amount of *Streptococcus thermophilus* TCI633 strain and/or its metabolites. In the method according to the present invention, the applied route, applied form, suitable dosage and use of the *Streptococcus thermophilus* TCI633 strain and/or its metabolites are all in line with the above description.

The present invention will be further illustrated in detail with specific examples as follows. However, the following examples are provided only for illustrating the present invention and the scope of the present invention is not limited thereby. The scope of the present invention will be indicated in the appended claims.

EXAMPLES

[Experimental Materials]

The resources of materials, agents and machines used in the examples are as follows:
(1) MRS medium: purchased from BD, product number 288130.
(2) X-VIVO 10 medium: purchased from Lonza Company.
(3) TRIzol® agent: purchased from Invitrogen Company.
(4) NanoDrop 1000 spectrophotometer: purchased from Thermo Fisher Scientific Company.
(5) Human Whole Genome OneArray®: purchase from Phalanx Biotech Group.
(6) DNA Microarray Scanner: purchased from Agilent Technologies Company, model G2505C.
(7) GenePix 4.1 software: purchased from Molecular Device Company.
(8) Rosetta Resover System®: purchased from Rosetta Biosoftware Company.
(9) Alpha-MEM medium: purchased from Gibco Company, product number 12000-022.
(10) FBS: purchased from Gibco Company.
(11) P/S (Penicillin/Streptomycin): purchased from Gibco Company.
(12) Human RANKL: purchased from Peprotech Company, product number 310-01.
(13) Human M-CSF: purchased from Peprotech Company, product number 300-25.
(14) Actin Green™ 488 ReadyProbes® agent: purchased from Thermo Company, product number R37110.
(15) Hoechst 33342 agent: purchased from Thermo Company, product number 62249.

Preparation Examples

A. Harvest of Peripheral Blood Mononuclear Cells (PBMCs)

PBMCs are immunocytes present in the peripheral blood. In this preparation example, PBMCs were isolated from the peripheral blood obtained from healthy donors.

B. Preparation of *Streptococcus thermophilus* TCI633 Strain Fermentation Supernatant

*Streptococcus thermophilus* TCI633 strain was statically cultivated in a MRS medium at 37° C. for 15 hours, and then the medium was centrifuged (rotational speed: 5000 rpm; time: 40 minutes) to remove most of the bacteria. The supernatant of the centrifuged medium was then filtered with 0.2 μm filter to further remove the bacteria. Thereafter, the supernatant was collected from the above centrifuged and filtered medium, and thus *Streptococcus thermophilus* TCI633 strain fermentation supernatant was obtained. The TCI633 strain fermentation supernatant was stored at −20° C. for the following experiments.

Example 1: Effects of *Streptococcus thermophilus* TCI633 Strain and its Metabolites on Inhibiting Osteoclast Activation and Differentiation (1-1) Inhibition of Expressions of the Osteoclast Activation and Differentiation-Related Genes It is known that genes such as CTSK, TRAP, c-FOS, MITF, BLNK and SYK are related to the osteoclast activation and differentiation. If the expression level of the above genes can be inhibited, the osteoclast activation and differentiation can be inhibited, and thus, the effects of preventing and/or treating osteoporosis can be achieved.

To know whether *Streptococcus thermophilus* TCI633 strain and its metabolites have effects on inhibiting osteoclast activation and differentiation, PBMCs obtained from [Preparation Examples A] were divided into four groups and treated as follows under 5% $CO_2$ at 37° C.:
(A) "Control group": cells were cultivated in X-VIVO 10 medium (i.e., a medium free of TCI633 strain fermentation supernatant) for 24 hours;
(B) "3 hours group": cells were treated as the "control group," but after the cells had been cultivated in X-VIVO 10 medium for 21 hours, TCI633 strain fermentation supernatant provided by [Preparation Examples B] was added into the medium to provide a final concentration of 2%, and then the cultivation was conducted for another 3 hours;

(C) "6 hours group": cells were treated as the "control group," but after the cells had been cultivated in X-VIVO 10 medium for 18 hours, TCI633 strain fermentation supernatant provided by [Preparation Examples B] was added into the medium to provide a final concentration of 2%, and then the cultivation was conducted for another 6 hours;

(D) "24 hours group": cells were treated as the "control group," but TCI633 strain fermentation supernatant provided by [Preparation Examples B] was added into the X-VIVO 10 medium to provide a final concentration of 2% before conducting the cultivation.

Thereafter, the PBMCs of the above groups were harvested and subjected to RNA extraction and purification as following the TRIzol® Reagent manufacturers' instructions, and then a NanoDrop 1000 spectrophotometer was used to measure the ratios of OD260/OD280 and OD260/OD230 of the obtained RNA. The RNA was then treated as follows:

(1) 1 μg of RNA was used to synthesize the first strand cDNA through reverse transcription;
(2) The first strand cDNA obtained from step 1 was used to synthesize the second strand cDNA, and then the double strand cDNA was purified;
(3) The double strand cDNA obtained from step 2 was used to synthesize the amino Allyl-modified aRNA through the transcription, and then the aRNA was purified;
(4) Cy5 fluorescent dye was used for performing the dye coupling reaction on the purified-aRNA, and then the dye-labeled aRNA was purified;
(5) The dye-labeled aRNA obtained from step 4 was hybridized to the Human Whole Genome OneArray® with Phalanx hybridization buffer and Phalanx Hybridization System;
(6) After 16 hours of hybridization, non-specific binding targets were washed away;
(7) The microarray was screened with a DNA Microarray Scanner;
(8) The Cy5 fluorescent intensities of each spot were analyzed with GenePix 4.1 software; and
(9) Steps 5 to 8 were repeated at least twice in each single sample with a reproducibility more than 0.975, and then the average values of signal intensities were loaded into the Rosetta Resolver System®.

Thereafter, the expression levels of the genes related to osteoclast activation and differentiation (including CTSK, TRAP, c-FOS, MITF, BLNK and SYK) in each group (including the "control group," "3 hours group," "6 hours group" and "24 hours group") were recorded. The gene expression levels of each experimental groups were normalized by using that of the control group as a basis. The results are shown in FIG. 1.

As shown in FIG. 1, as compared to the control group, the expression levels of genes such as CTSK, TRAP, c-FOS, MITF, BLNK and SYK in the "3 hours group," "6 hours group" and "24 hours group" all significantly decreased. The above results indicate that the TCI633 strain fermentation supernatant is effective in inhibiting osteoclast activation and differentiation, and thus, can be used for preventing and/or treating osteoporosis.

(1-2) Expression of Actin

It is known that non-differentiated PBMCs is smaller in volume and the actin therein will express all over the cell, and thus dotted fluorescence could be observed if actin staining is conducted. PBMCs, after being stimulated by osteoclast differential factors, would fuse to form osteoclasts that is larger in volume and has multiple nuclei. In addition, actin in the osteoclast will form a significant ring-like structure at the edge of cell. Thus, if actin staining is conducted on the cells at this time, ring-like fluorescence can be seen.

PBMCs obtained from [Preparation Examples A] were divided into four groups and treated as follows under 5% $CO_2$ at 37° C.:

(A) Control group: cells were cultivated in an Alpha-MEM medium for 14 days;
(B) Differentiation group: cells were subjected to the operation as the "control group," but osteoclast differentiation medium (i.e., an Alpha-MEM medium added with 10% FBS, 1×P/S, human RANKL (40 ng/ml) and human M-CSF (25 ng/ml)) was adopted to conduct the cultivation;
(C) Empty medium group: cells were subjected to the operation as the "differentiation group," but the adopted osteoclast differentiation medium was added with empty medium (i.e., 1% MRS medium); and
(D) Supernatant group: cells were subjected to the operation as the "differentiation group," but the adopted osteoclast differentiation medium was added with 1% TCI633 strain fermentation supernatant provided by [Preparation Examples B].

Thereafter, cells of each group were stained by Actin Green™ 488 ReadyProbes® and Hoechst 33342 agents (1:20000 diluted) for 15 minutes. The staining results are shown in FIG. 2, wherein the yellow fluorescence represents actin, and the blue fluorescence represents the nucleus.

Figure 2:
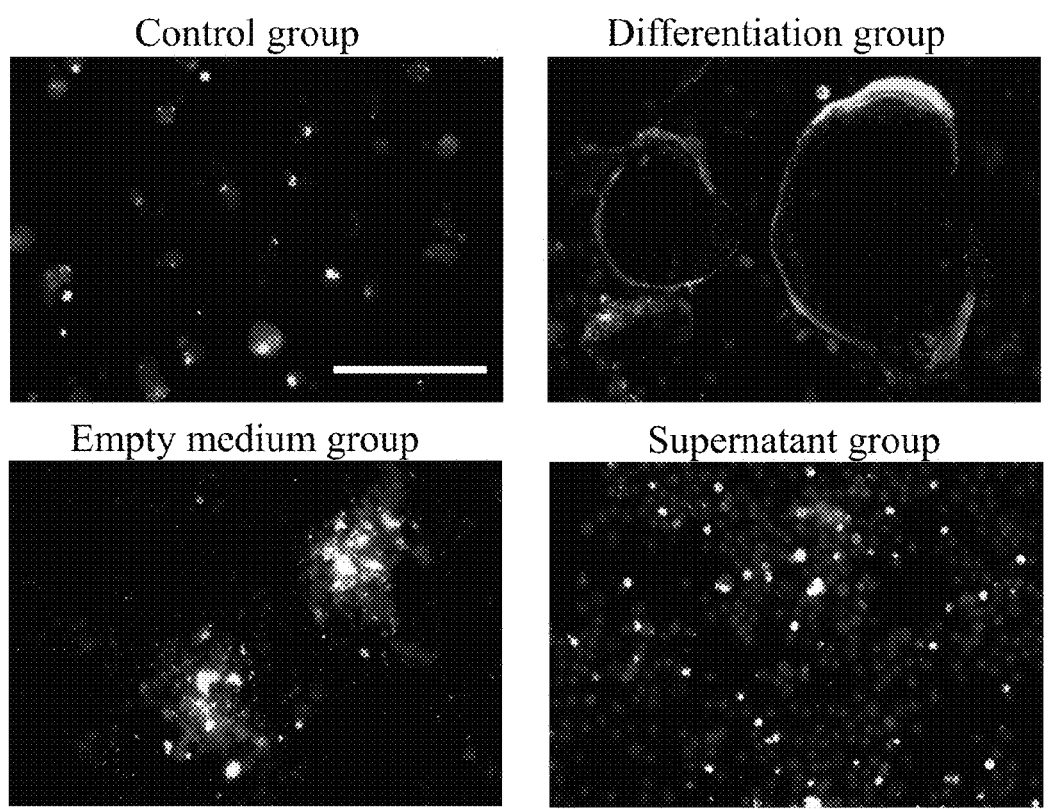
FIG. 2 is the result of the immune-fluorescent staining (the yellow fluorescence represents actin; the blue fluorescence represents nucleus; and the scar bar is 100 µm), showing the differentiation levels (differentiating into osteoclasts) of PBMCs obtained from different groups, wherein the "control group" was cultivated in a medium free of TCI633 strain fermentation supernatant, the "differentiation group" was cultivated in an osteoclast differentiation medium, the "empty medium group" was cultivated in an osteoclast differentiation medium added with empty medium (i.e., MRS medium), and the "supernatant group" was cultivated in an osteoclast differentiation medium added with TCI633 strain fermentation supernatant.

As shown in FIG. 2, the distribution of actin in the differentiation group was significantly ring-like. As compared to the differentiation group and empty medium group, the distribution of actin in the supernatant group was significantly more like the control group. The above results indicate that *Streptococcus thermophilus* TCI633 strain fermentation supernatant is effective in inhibiting the differentiation of PBMCs into osteoclasts, and illustrate again that *Streptococcus thermophilus* TCI633 strain and its metabolites can be used for preventing and/or treating osteoporosis.

As shown in the above experiments, *Streptococcus thermophilus* TCI633 strain and its metabolites of the present invention is effective in inhibiting osteoclast activation and differentiation, and thus, can be used for preventing and/or treating osteoporosis and then reaching the effects of delaying bone loss, increasing bone density, and/or strengthening bones.

DEPOSIT OF BIOLOGICAL MATERIAL

Depository institute: DE Germany German Collection of Microorganisms and Cell Cultures (Deutsche Sammlung von Mikroorganismen and Zellkulturen GmbH, DSMZ); Address: Inhoffenstraβe 7 B, 38124 Braunschweig, GERMANY; Date: 2013 Dec. 2; Accession number: DSM 28121.

What is claimed is:

1. A method of preventing osteoporosis, comprising administering to a subject in need an effective amount of *Streptococcus thermophilus* TCI633 strain and/or its metabolites, wherein the *Streptococcus thermophilus* TCI633 strain was deposited at German Collection of Microorganisms and Cell Cultures (Deutsche Sammlung von Mikroorganismen und Zellkulturen GmbH, DSMZ) under the accession number DSM 28121.

2. The method as claimed in claim 1, wherein the *Streptococcus thermophilus* TCI633 strain and/or its metabolites inhibit osteoclast activation.

3. The method as claimed in claim 1, wherein the *Streptococcus thermophilus* TCI633 strain and/or its metabolites inhibit osteoclast differentiation.

4. The method as claimed in claim 1, wherein the *Streptococcus thermophilus* TCI633 strain and its metabolites are administered to the subject by oral administration.

5. A method of treating osteoporosis, comprising administering to a subject in need an effective amount of *Streptococcus thermophilus* TCI633 strain and/or its metabolites, wherein the *Streptococcus thermophilus* TCI633 strain was deposited at German Collection of Microorganisms and Cell Cultures (Deutsche Sammlung von Mikroorganismen und Zellkulturen GmbH, DSMZ) under the accession number DSM 28121.

6. The method as claimed in claim 5, wherein the *Streptococcus thermophilus* TCI633 strain and/or its metabolites inhibit osteoclast activation.

7. The method as claimed in claim 5, wherein the *Streptococcus thermophilus* TCI633 strain and/or its metabolites inhibit osteoclast differentiation.

8. The method as claimed in claim 5, wherein the *Streptococcus thermophilus* TCI633 strain and its metabolites are administered to the subject by oral administration.

9. A method of at least one of delaying bone loss, increasing bone density, and strengthening bones, comprising administering to a subject in need an effective amount of *Streptococcus thermophilus* TCI633 strain and/or its metabolites, wherein the *Streptococcus thermophilus* TCI633 strain was deposited at German Collection of Microorganisms and Cell Cultures (Deutsche Sammlung von Mikroorganismen and Zellkulturen GmbH, DSMZ) under the accession number DSM 28121.

10. The method as claimed in claim 9, wherein the *Streptococcus thermophilus* TCI633 strain and/or its metabolites inhibit osteoclast activation.

11. The method as claimed in claim 9, wherein the *Streptococcus thermophilus* TCI633 strain and/or its metabolites inhibit osteoclast differentiation.

12. The method as claimed in claim 9, wherein the *Streptococcus thermophilus* TCI633 strain and its metabolites are administered to the subject by oral administration.

* * * * *